US009788807B2

(12) United States Patent
Schmitt et al.

(10) Patent No.: US 9,788,807 B2
(45) Date of Patent: Oct. 17, 2017

(54) PROCESSING APPARATUS FOR PROCESSING CARDIAC DATA (71) Applicant: KONINKLIJKE PHILIPS N.V., Eindhoven (NL)

(72) Inventors: Holger Schmitt, Luetjensee (DE); Hannes Nickisch, Hamburg (DE); Sven Prevrhal, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/912,241

(22) PCT Filed: Aug. 26, 2014

(86) PCT No.: PCT/EP2014/068016
§ 371 (c)(1),
(2) Date: Feb. 16, 2016

(87) PCT Pub. No.: WO2015/032647
PCT Pub. Date: Mar. 12, 2015

(65) Prior Publication Data
US 2016/0206265 A1    Jul. 21, 2016

(30) Foreign Application Priority Data
Sep. 6, 2013   (EP) .................... 13183330

(51) Int. Cl.
*A61B 6/00*   (2006.01)
*A61B 6/03*   (2006.01)
*G06T 7/254*  (2017.01)

(52) U.S. Cl.
CPC .............. *A61B 6/503* (2013.01); *A61B 6/032* (2013.01); *A61B 6/461* (2013.01); *A61B 6/504* (2013.01);
(Continued)

(58) Field of Classification Search
CPC ......... A61B 6/503; A61B 6/032; A61B 6/461; A61B 6/504; A61B 6/507; A61B 6/5217;
(Continued)

(56) References Cited

U.S. PATENT DOCUMENTS 7,790,142 B2 * 9/2010 Elmaleh ............ A61K 51/0402
424/1.11
7,840,255 B2 * 11/2010 Ichihara ................ A61B 6/481
600/407

(Continued)

FOREIGN PATENT DOCUMENTS

DE    102008014792    6/2009
WO    2004025572      3/2004
(Continued)

OTHER PUBLICATIONS

Melikian et al., 2009, "Fractional Flow Reserve and Myocardial Perfusion Imaging in Patients With Angiographic Multivessel Coronary Artery Disease", (pp. 307-314).*

(Continued)

*Primary Examiner* — Manav Seth (57) ABSTRACT

The invention relates to a processing apparatus for processing cardiac data of a living being and to an imaging system comprising the processing apparatus. A distribution of Fractional flow reserve (FFR) values being indicative of the FFR of different coronary arteries of the living being, a distribution of myocardial perfusion values like values of an iodine map being indicative of the myocardial perfusion of different portions of the myocardium of the living being and assignments between coronary arteries and portions of the myocardium of the living being are used for determining degrees of correspondence between FFR values and myocardial perfusion values. This allows for, for example, a determination of the reliability of the FFR values, if the (Continued)

myocardial perfusion values are known to be reliable, based on the determined degrees of correspondence.

15 Claims, 4 Drawing Sheets

(52) U.S. Cl.
CPC ............ *A61B 6/507* (2013.01); *A61B 6/5217* (2013.01); *G06T 7/254* (2017.01); *A61B 6/463* (2013.01); *A61B 6/466* (2013.01); *G06T 2207/10081* (2013.01); *G06T 2207/30048* (2013.01); *G06T 2207/30104* (2013.01)

(58) Field of Classification Search
CPC ....... A61B 6/463; A61B 6/466; A61B 6/5229; A61B 5/021; A61B 5/026; A61B 2576/023; G06T 7/254; G06T 2207/10081; G06T 2207/30048; G06T 2207/30101; G06T 2207/30104; G01R 33/56366

See application file for complete search history.

(56) References Cited

U.S. PATENT DOCUMENTS

| | | | | |
|---|---|---|---|---|
| 8,157,742 | B2* | 4/2012 | Taylor | A61B 5/02007 600/481 |
| 8,200,466 | B2 | 6/2012 | Spilker | |
| 8,249,815 | B2 | 8/2012 | Taylor | |
| 8,553,832 | B2* | 10/2013 | Camus | A61B 6/481 378/4 |
| 8,861,820 | B2* | 10/2014 | Fonte | G06T 7/0012 382/128 |
| 8,871,179 | B2* | 10/2014 | Elmaleh | A61K 51/0402 424/1.11 |
| 2005/0277830 | A1* | 12/2005 | Ichihara | A61B 6/481 600/425 |
| 2009/0208078 | A1 | 8/2009 | Fritz et al. | |
| 2010/0130878 | A1 | 5/2010 | Lasso | |
| 2010/0241404 | A1 | 9/2010 | Taylor | |
| 2011/0307231 | A1 | 12/2011 | Kirchner | |
| 2012/0022843 | A1 | 1/2012 | Ionasec | |
| 2012/0041318 | A1 | 2/2012 | Taylor | |
| 2012/0041319 | A1 | 2/2012 | Taylor | |
| 2012/0041320 | A1 | 2/2012 | Taylor | |
| 2012/0041321 | A1 | 2/2012 | Taylor | |
| 2012/0041322 | A1 | 2/2012 | Taylor | |
| 2012/0041323 | A1 | 2/2012 | Taylor | |
| 2012/0041735 | A1 | 2/2012 | Taylor | |
| 2012/0041739 | A1 | 2/2012 | Taylor | |
| 2012/0053918 | A1* | 3/2012 | Taylor | A61B 5/02007 703/9 |
| 2012/0053919 | A1 | 3/2012 | Taylor | |
| 2012/0059246 | A1 | 3/2012 | Taylor | |
| 2012/0072190 | A1 | 3/2012 | Sharma | |
| 2012/0121151 | A1 | 5/2012 | Bernhardt | |
| 2012/0243761 | A1 | 9/2012 | Senzig | |
| 2013/0121163 | A1 | 5/2013 | Ehrlich et al. | |
| 2013/0132054 | A1 | 5/2013 | Sharma et al. | |

FOREIGN PATENT DOCUMENTS

| | | |
|---|---|---|
| WO | 2006061814 | 6/2006 |
| WO | 2006061815 | 6/2006 |
| WO | 2010022762 | 3/2010 |

OTHER PUBLICATIONS

Roessl, et al., "K-edge imaging in x-ray computed tomography using multi-bin photon counting detectors", Physics in Medicine and Biology, vol. 52, pp. 4679 to 4696, 2007.

Miles, et al., "Perfusion CT: a worthwhile enhancement?", British Journal of Radiology, vol. 76, pp. 220-231, 2003.

P. Beliveau, et al., "Computation of coronary perfusion territories from CT angiography", Computers in Cardiology, vol. 34, pp. 753-756, 2007.

Ko, et al., "Combined CT coronary angiography and stress myocardial perfusion imaging for hemodynamically significant stenoses in patients with suspected coronary artery disease: a comparison with fractional flow reserve", JACC. Cardiovascular imaging, Nov. 1, 2012.

Watkins, et al., "Validation of Magnetic Resonance Myocardial Perfusion Imaging with Fractional Flow Reserve for the Detection of Significant Coronary Heart Disease", American Heart Association, Nov. 16, 2009.

Melikian, et al., "Fractional Flow Reserve and Myocardial Perfusion Imaing in Patients with Angiographical Multivessel Coronary Artery Disease", vol. 3, No. 3, 2010.

* cited by examiner

PROCESSING APPARATUS FOR PROCESSING CARDIAC DATA

CROSS REFERENCE TO RELATED APPLICATIONS

This application is the U.S. National Phase application under 35 U.S.C. §371 of International Application No. PCT/EP2014/068016, filed Aug. 26, 2014, published as WO 2015/032647 on Mar. 12, 2015, which claims the benefit of European Patent Application Number 13183330.3 filed Sep. 6, 2013. These applications are hereby incorporated by reference herein.

FIELD OF THE INVENTION

The invention relates to a processing apparatus, a processing method and a computer program for processing cardiac data of a living being. The invention relates further to an imaging system for imaging a heart of a living being, which comprises the processing apparatus. The invention relates also to a corresponding imaging method and computer program for imaging a heart of a living being.

BACKGROUND OF THE INVENTION

US 2013/0132054 A1 discloses an apparatus comprising an anatomical model generating unit for generating a patient-specific anatomical model of coronary arteries and the heart from medical image data of a patient and a functional model generating unit for generating a multi-scale functional model of coronary circulation based on the patient-specific anatomical model. The apparatus further comprises a simulation unit for simulating blood flow in at least one stenosis region of at least one coronary artery using the multi-scale functional model of coronary circulation. The simulation unit is particularly adapted to calculate hemodynamic quantities like fractional flow reserve (FFR) values for the at least one stenosis region.

The calculated hemodynamic quantities can be unreliable, which in turn can lead to an unreliable assessment of the at least one stenosis region based on the unreliable calculated hemodynamic quantities.

SUMMARY OF THE INVENTION

It is an object of the present invention to provide a processing apparatus, a processing method and a computer program for processing cardiac data of a living being, which allows for an assessment of the reliability of calculated hemodynamic quantities. It is a further object of the present invention to provide an imaging system for imaging a heart of a living being, which comprises the processing apparatus, and to provide a corresponding imaging method and a corresponding computer program for imaging the heart of the living being.

In a first aspect of the present invention a processing apparatus for processing cardiac data of a living being is presented, wherein the processing apparatus comprises:
  an FFR providing unit for providing a distribution of FFR values being indicative of the FFR of different coronary arteries of the living being,
  a myocardial perfusion providing unit for providing a distribution of myocardial perfusion values being indicative of the myocardial perfusion of different portions of the myocardium of the living being,
  an assignments providing unit for providing assignments between coronary arteries and portions of the myocardium of the living being, wherein the assignments define which portion of the myocardium is fed by which coronary artery,
  a correspondence determining unit for determining degrees of correspondence between FFR values and myocardial perfusion values based on the distribution of FFR values, the distribution of myocardial perfusion values and the assignments between the coronary arteries and portions of the myocardium.

Since the coronary arteries feed the myocardium, an FFR value provided for, for instance, one or several coronary arteries should correspond to a myocardial perfusion value provided for a portion of the myocardium, which is fed by the one or several coronary arteries, if the FFR value provided for the one or several coronary arteries and the myocardium value provided for the respective portion of the myocardium are reliable. For instance, if the FFR value provided for the one or several coronary arteries and the myocardial perfusion value provided for a portion of the myocardium, which is fed by the one or several coronary arteries, are both relatively large or both relatively low, i.e. if they have a relatively large degree of correspondence, it can be assumed that the FFR value and the myocardial perfusion value have a relative large reliability. If the degree of correspondence is relatively low, i.e., for instance, if one of these values is relatively large and the other of these values is relatively small, it can be assumed that the reliability of at least one of these values is relatively small.

In particular, if the myocardial perfusion values are known to be reliable, the determined degrees of correspondence between the FFR values and the myocardial perfusion values indicate the degree of reliability of the FFR values. If the FFR values are known to be reliable, the determined degrees of correspondence between the FFR values and the myocardial perfusion values indicate the degree of reliability of the myocardial perfusion values.

It is preferred that the FFR providing unit is adapted to determine the distribution of FFR values based on a provided three-dimensional geometry of the coronary artery tree. Preferentially, a three-dimensional computed tomography angiography (CTA) image is used for providing the three-dimensional geometry of the coronary artery tree. The FFR providing unit is preferentially adapted to simulate the flow of the blood in the coronary arteries based on the three-dimensional geometry of the coronary artery tree for determining the FFR values.

It is further preferred that the processing apparatus comprises a heart model providing unit for providing a cardiac model, wherein the cardiac model models at least different portions of the myocardium fed by different coronary arteries, wherein the assignments providing unit is adapted to register the cardiac model to the provided three-dimensional geometry of the coronary artery tree for determining the assignments between coronary arteries and portions of the myocardium. In particular, the heart model providing unit may be configured to adapt a standard cardiac model to an image of the heart of the living being, in order to provide an individualized cardiac model, which can be used for determining the assignments between coronary arteries and portions of the myocardium. The standard heart model may be a heart model defined by the American Heart Association.

The myocardial perfusion providing unit is preferentially adapted to provide a three-dimensional iodine map obtained from a spectral CT measurement or an area-under-curve map obtained from a dynamic myocardial perfusion CT measurement as the distribution of myocardial perfusion values. These myocardial perfusion values are generally very reliable such that the determined degree of correspondence can be used to indicate the degree of reliability of the FFR values.

The correspondence determining unit can be adapted to determine the degrees of correspondence between FFR values and myocardial perfusion values based on predefined correspondence rules, wherein the correspondence rules define a degree of correspondence between an FFR value provided for one or several coronary arteries and a myocardial perfusion value of a portion of the myocardium fed by the one or several coronary arteries based on the FFR value and the myocardial perfusion value. In particular, the distribution of FFR values may define an FFR value for one or several coronary arteries assigned to the same portion of the myocardium and the distribution of myocardial perfusion values may define a myocardial perfusion value for the portion of the myocardium, wherein the correspondence determining unit can be adapted to determine a degree of correspondence between the FFR value and the myocardial perfusion value by comparing the FFR value with a first threshold and the myocardial perfusion value with a second threshold, wherein the correspondence rules can define that i) a larger degree of correspondence is determined, if a) the FFR value is smaller than the first threshold and the myocardial perfusion value is smaller than the second threshold or b) the FFR value is larger than the first threshold and the myocardial perfusion value is larger than the second threshold, and ii) a smaller degree of correspondence is determined, if a) the FFR value is larger than the first threshold and the myocardial perfusion value is smaller than the second threshold or b) the FFR value is smaller than the first threshold and the myocardial perfusion value is larger than the second threshold. The first threshold may depend on the distribution of FFR values and/or the second threshold may depend on the distribution of myocardial perfusion values. In particular, the first threshold may depend on the average of the distribution of FFR values and/or the second threshold may depend on the average of the distribution of myocardial perfusion values. However, the first threshold and/or the second threshold may also be predetermined.

The distribution of FFR values can directly define a respective FFR value for each coronary artery, wherein the FFR value for one or several coronary arteries assigned to the same portion of the myocardium can be defined by the FFR values assigned to the respective one or several coronary arteries. In particular, if the respective portion of the myocardium is fed by several coronary arteries, the FFR values defined for these coronary arteries can be combined, for instance, averaged, for determining a single FFR value for these coronary arteries. However, the distribution of FFR values can also indirectly define for each coronary artery an FFR value, wherein in this case the distribution may provide FFR values distributed along the length of the respective coronary artery and wherein these FFR values distributed along the length of the respective coronary artery define a single FFR value of the respective coronary artery, which may be determined by combining the FFR values distributed along the length of the respective coronary artery, in particular, by multiplying the FFR values.

The distribution of myocardial perfusion values can directly define a respective myocardial perfusion value for each portion of the myocardium. However, the distribution of myocardial perfusion values can also indirectly define for each portion of the myocardium a myocardial perfusion value, wherein in this case the distribution may provide myocardial perfusion values distributed within the respective portion of the myocardium and wherein these myocardial perfusion values distributed within the respective portion of the myocardium define a single myocardial perfusion value of the respective portion of the myocardium, which may be determined by combining the myocardial perfusion values distributed within the respective portion of the myocardium, in particular, by averaging the myocardial perfusion values.

The processing apparatus preferentially comprises a display for displaying the coronary arteries and/or the portions of the myocardium and for displaying indications being indicative of the determined degrees of correspondence at the respective locations of the coronary arteries and/or of the portions of the myocardium, respectively. In particular, the processing apparatus may be adapted such that i) a first kind of indications is shown on the display at locations of the coronary arteries and/or of the portions of the myocardium, at which the respective determined degree of correspondence is smaller than a correspondence threshold, and/or ii) a second kind of indications is shown on the display at locations of the coronary arteries and/or of the portions of the myocardium, at which the respective determined degree of correspondence is larger than the correspondence threshold. For instance, regions, for which a degree of correspondence has been determined, which is smaller than a correspondence threshold, can be encircled on the display, in order to indicate to the user regions comprising unreliable values. The correspondence threshold can be predetermined based on, for instance, calibration procedures, in which FFR values and/or myocardial perfusion values are provided, which are known to be reliable or unreliable, and wherein the correspondence threshold is chosen such that at locations of the coronary arteries and/or of the portions of the myocardium, at which the values are reliable, the second kind of indications is shown, and at locations of the coronary arteries and/or of the portions of the myocardium, at which the values are unreliable, the first kind of indications is shown. This allows a user to readily grasp at which locations the values are reliable and at which locations the values are not reliable.

In an embodiment the FFR providing unit is adapted to determine the distribution of FFR values based on a first image of the heart of the living being generated by a first imaging modality and the myocardial perfusion providing unit is adapted to determine the distribution of myocardial perfusion values based on a second image of the heart of the living being generated by a second imaging modality being different to the first imaging modality. Thus, the processing apparatus can also be adapted to determine the correspondence between FFR values and myocardial perfusion values, which have been determined based on images generated by different imaging modalities. However, in another embodiment the FFR values and the myocardial perfusion values may have been determined based on images generated by the same imaging modality.

In a further aspect of the present invention an imaging system for imaging a heart of a living being is presented, wherein the imaging system comprises:
  an image generation device for generating a first image of the heart being indicative of the FFR of different coronary arteries of the living being and for generating a second image of the heart being indicative of the myocardial perfusion of different portions of the myocardium of the living being,
  a processing apparatus as defined in claim 1, wherein the FFR providing unit is adapted to determine the distribution of FFR values based on the first image and wherein the myocardial perfusion providing unit is adapted to determine the distribution of myocardial perfusion values based on the second image, a display for displaying the coronary arteries and/or the portions of the myocardium and for displaying indications being indicative of the determined degrees of correspondence at the respective locations of the coronary arteries and/or of the portions of the myocardium, respectively.

The first image of the heart can be any image of the heart, which allows determining the FFR of different coronary arteries of the living being. In particular, the first image can be any anatomical image, which shows the geometry of the coronary arteries and/or from which the geometry of the coronary arteries can be derived, wherein the FFR providing unit can be adapted to determine the FFR values based on the geometry of the coronary arteries. Correspondingly, the second image can be any image which shows the myocardial perfusion values or which allows determining the myocardial perfusion values. In a further aspect of the present invention a processing method for processing cardiac data of a living being is presented, wherein the processing method comprises:

providing a distribution of FFR values being indicative of the FFR of different coronary arteries of the living being, providing a distribution of myocardial perfusion values being indicative of the myocardial perfusion of different portions of the myocardium of the living being, providing assignments between coronary arteries and portions of the myocardium of the living being, wherein the assignments define which portion of the myocardium is fed by which coronary artery, determining degrees of correspondence between FFR values and myocardial perfusion values based on the distribution of FFR values, the distribution of myocardial perfusion values and the assignments between the coronary arteries and portions of the myocardium.

In a further aspect of the present invention an imaging method for imaging a heart of a living being is presented, wherein the imaging method comprises:

generating a first image of the heart being indicative of the FFR of different coronary arteries of the living being and generating a second image of the heart being indicative of the myocardial perfusion of different portions of the myocardium of the living being, determining degrees of correspondence between FFR values and myocardial perfusion values as defined in claim 12, wherein the distribution of FFR values is provided by determining FFR values based on the first image and the distribution of myocardial perfusion values is provided by determining myocardial perfusion values based on the second image, displaying the coronary arteries and/or the portions of the myocardium and displaying indications being indicative of the determined degrees of correspondence at the respective locations of the coronary arteries and/or of the portions of the myocardium, respectively.

In a further aspect of the present invention a computer program for processing cardiac data of a living being is presented, wherein the computer program comprises program code means for causing a processing apparatus as defined in claim 1 to carry out the steps of the processing method as defined in claim 12, when the computer program is run on a computer controlling the processing apparatus.

In a further aspect of the present invention a computer program for imaging a heart of a living being is presented, wherein the computer program comprises program code means for causing an imaging system as defined in claim 11 to carry out the steps of the imaging method as defined in claim 13, when the computer program is run on a computer controlling the processing apparatus.

It shall be understood that the processing apparatus of claim 1, the imaging system of claim 11, the processing method of claim 12, the imaging method of claim 13, the computer program of claim 14 and the computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
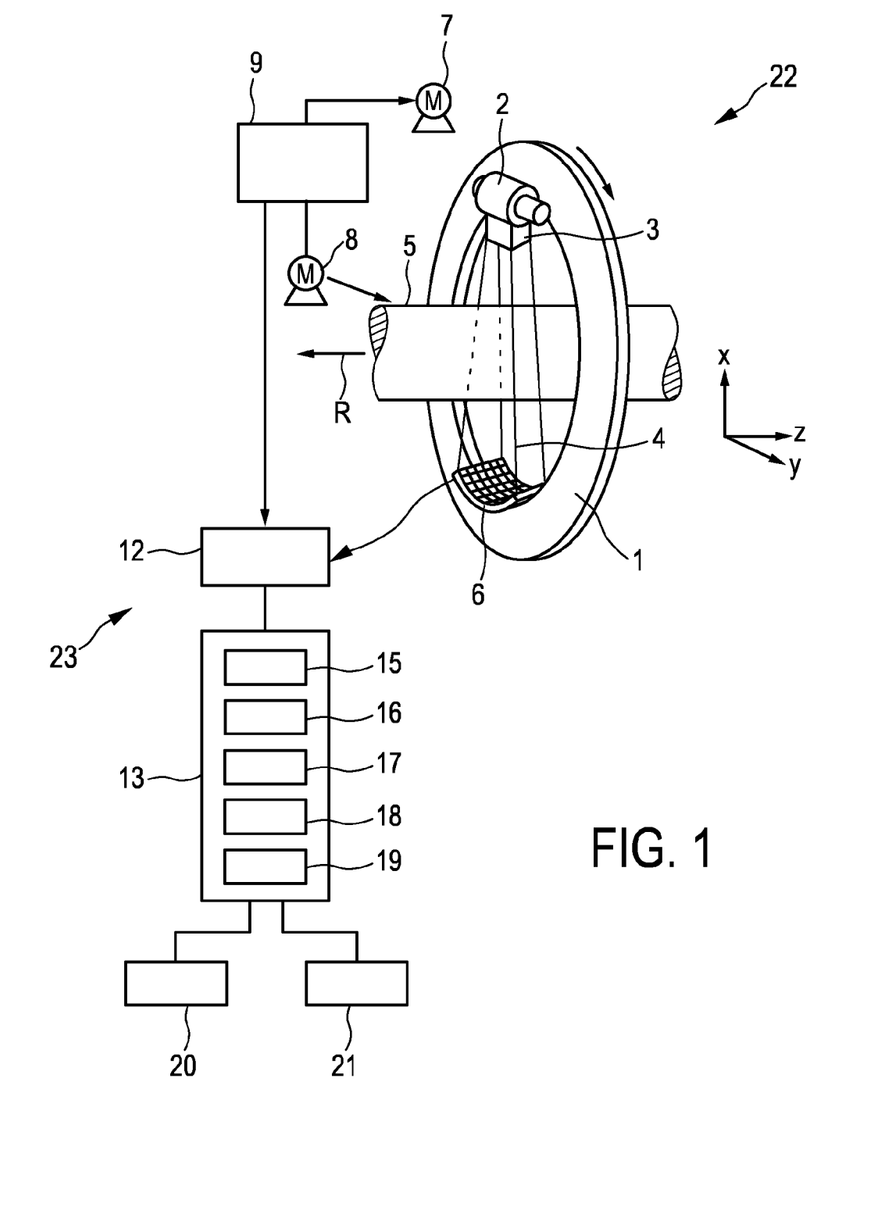
FIG. 1 schematically and exemplarily shows an embodiment of an imaging system for imaging a heart of a living being, FIG. 2 schematically and exemplarily shows a distribution of FFR values, FIG. 3 schematically and exemplarily shows a distribution of myocardial perfusion values, FIG. 4 schematically and exemplarily shows a cardiac model.

FIG. 1 shows schematically and exemplarily an embodiment of an imaging system for imaging a heart of a living being. In this embodiment the imaging system 22 is a CT system and the living being is a person arranged on a patient table (not shown for clarity reasons) within an examination zone 5. The imaging system 22 comprises an image generation device 23 for generating a first image of the heart being indicative of the FFR of different coronary arteries of the person and for generating a second image of the heart being indicative of the myocardial perfusion of different portions of the myocardium of the person. In particular, the image generation device 23 of the CT system 22 comprises a gantry 1 which is capable of rotation about a rotational axis R that extends parallel to a z direction. An x-ray tube 2 provided with a collimator 3 for generating, in this embodiment, a conical radiation beam 4 is mounted on the gantry 1. The radiation beam 4 traverses the heart of the person within the examination zone 5, wherein, after having traversed the heart of the person, the radiation beam 4 is incident on an x-ray detector 6 comprising, in this embodiment, a two-dimensional detection surface. Also the x-ray detector 6 is mounted on the gantry 1.

The image generation device 23 further comprises two motors 7, 8, wherein the gantry 1 is driven at a preferably constant but adjustable angular speed by the motor 7, and the motor 8 is provided for displacing the person, who may be arranged on a patient table, within the examination zone 5 parallel to the direction of the rotational axis R or the z axis. These motors are controlled by a control unit 9, for instance, such that the x-ray source 2 and the x-ray detector 6 move along a circular or a helical trajectory relative to the heart of the person. In another embodiment the collimator 3 can be adapted for forming another beam shape, in particular, a fan beam, and the x-ray detector 6 can comprise a detection surface, which is shaped corresponding to the other beam shape, in particular to the fan beam.

During the movement of the x-ray source 2 and the x-ray detector 6 the x-ray detector 6 generates projection values depending on the radiation incident on the detection surface of the x-ray detector 6, which are provided to a reconstruction unit 12 for reconstructing the first and second images of the heart. The first and second images are provided to a processing apparatus 13.

The processing apparatus 13 comprises an FFR providing unit 15 for providing a distribution of FFR values being indicative of the FFR of different coronary arteries of the living being. In this embodiment the first image is a three-dimensional CTA image, which is used by the FFR providing unit 15 to determine the three-dimensional geometry of the coronary artery tree of the person. The FFR providing unit 15 simulates the flow of the blood in the coronary arteries based on the three-dimensional geometry of the coronary artery tree for determining the FFR values. For a more detailed description of the determination of the FFR values reference is made to, for instance, the article "In vivo flow simulation in coronary arteries based on CT datasets: feasibility and initial results" by Thomas Frauenfelder et al., European Radiology, 17(5), pages 1291 to 1300 (2007) and to US2012/0150516A1, which are herewith incorporated by reference. A coronary artery tree 24 including calculated FFR values is schematically and exemplarily shown in FIG. 2. Since the FFR values are calculated and not directly measured, they may be regarded as being virtual FFR values.

The processing apparatus 13 further comprises a myocardial perfusion providing unit 16 for providing a distribution of myocardial perfusion values being indicative of the myocardial perfusion of different portions of the myocardium of the living being. In this embodiment the image generation device 23 is adapted to generate a spectral CT image as the second image and to determine a three-dimensional iodine map based on the generated spectral CT image, in order to provide the distribution of myocardial perfusion values. The three-dimensional iodine map 25 is schematically and exemplarily shown in FIG. 3. In another embodiment, the distribution of myocardial perfusion values can be provided in another way. For instance, an area-under-curve map can be determined based on a second image being a dynamic myocardial perfusion CT image as the distribution of myocardial perfusion values.

Figure 3:
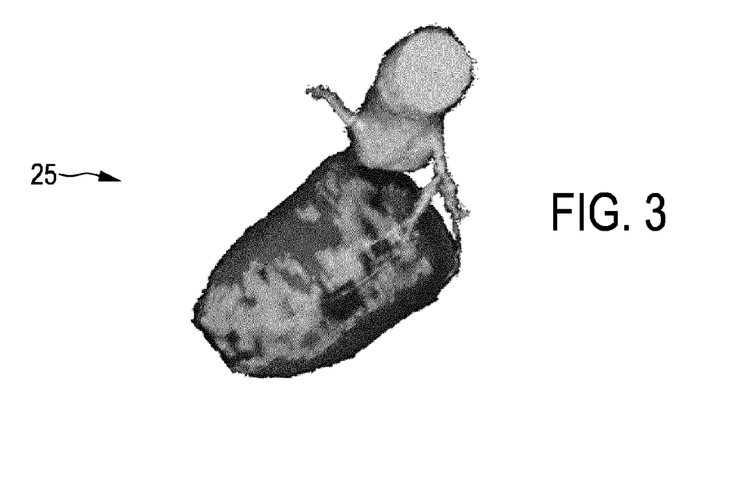

The voxel values of the iodine map are indicative of the amount of iodine deposited at the respective location and can therefore be regarded as being myocardial perfusion values. The iodine map can be determined based on K-edge imaging in spectral x-ray CT using multi-bin photon counting detectors as disclosed, for instance, in the article "K-edge imaging in x-ray computed tomography using multi-bin photon counting detectors" by E. Roessl et al., Physics in Medicine and Biology, volume 52, pages 4679 to 4696 (2007), which is herewith incorporated by reference.

A dynamic myocardial perfusion CT image can be generated by repeatedly scanning the heart, while an injected contrast material like iodine is washed in and washed out of the heart. For instance, the dynamic myocardial perfusion CT image can comprise 10 to 20 volumetric images acquired over a period of 5 to 30 seconds. An area-under-curve map can be determined based on the dynamic myocardial perfusion CT image by integrating for each voxel the voxel values over a time period during which the contrast material is washed in and washed out of the heart. More details regarding dynamic myocardial perfusion CT imaging are disclosed in, for instance, the article "Perfusion CT: a worthwhile enhancement?" by K. Miles et al., British Journal of Radiology, volume 76, pages 220 to 231 (2003), which is herewith incorporated by reference.

Figure 4:
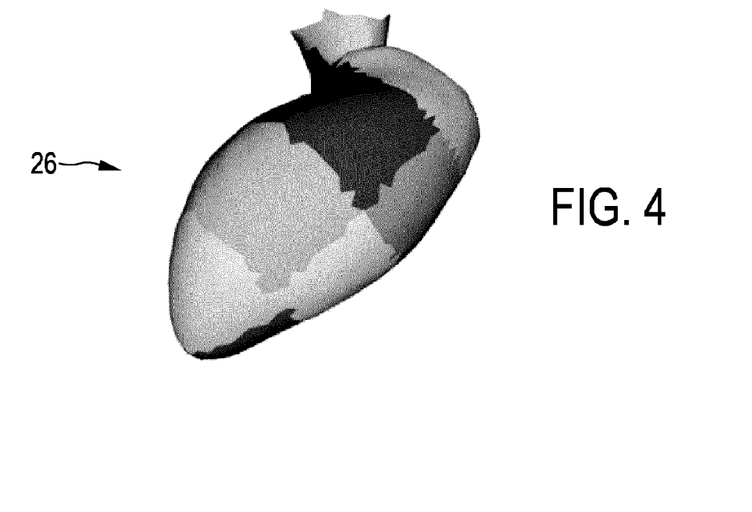

The processing apparatus 13 further comprises an assignments providing unit 18 for providing assignments between coronary arteries and portions of the myocardium of the person, wherein the assignments define which portion of the myocardium is fed by which one or several coronary arteries. In particular, a heart model providing unit 17 provides a cardiac model 26 modeling different portions of the myocardium being fed by different coronary arteries as schematically and exemplarily shown in FIG. 4, wherein the assignments providing unit 18 is adapted to register the cardiac model 26 to the provided three-dimensional geometry of the coronary artery tree for determining the assignments between coronary arteries and portions of the myocardium. The heart model providing unit 17 may be adapted to provide a standard cardiac model, which is not patient-specific, or the heart model providing unit 17 may be adapted to adapt a standard cardiac model to an actual image of the heart of the person generated by the image generation device 23 or by another image generation device, in order to provide a patient-specific cardiac model.

Figure 2:
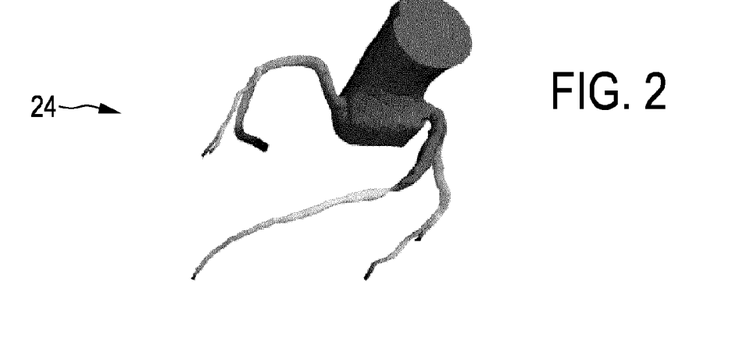

Thus, the assignments providing unit 18 can be adapted to map the individual coronary arteries to their feeding territories in the myocardium by using a model-based heart segmentation and, for instance, a standardized cardiac model like the standardized cardiac model defined by the American Heart Association. The assignments providing unit 18 provides the knowledge about which portion of the myocardium is fed by which one or several coronary arteries, in order to provide a geometric link between the distribution 24 of FFR values and the distribution 25 of myocardial perfusion values. The mapping algorithm is preferentially capable of handling individual variations of coronary configurations.

The assignments providing unit can also be adapted to use other methods for determining assignments between coronary arteries and portions of the myocardium of the person. For instance, the heart model providing unit can be adapted to provide a heart model with segmented portions of the myocardium, wherein this heart model can be registered to an actual image of the heart of the person, in order to determine the different portions of the myocardium of the person. In the actual image of the heart of the person also the coronary arteries may be detected and to each determined portion of the myocardium the one or several closest coronary arteries may be assigned. Also the assignment procedure disclosed in the article "Computation of coronary perfusion territories from CT angiography" by P. Beliveau et al., Computers in Cardiology, volume 34, pages 753 to 756 (2007) may be used, which is herewith incorporated by reference.

The processing apparatus further comprises a correspondence determining unit 19 for determining degrees of correspondence between FFR values and myocardial perfusion values based on the distribution 24 of the FFR values, the distribution 25 of the myocardial perfusion values and the assignments between the coronary arteries and the portions of the myocardium. The correspondence determining unit 19 can be adapted to determine the degrees of correspondence between the FFR values and the myocardial perfusion values based on predefined correspondence rules. In this embodiment an FFR value is determined for one or several coronary arteries assigned to the same portion of the myocardium by combining the FFR values of the distribution 24 of FFR values, which have been provided for these one or several coronary arteries. For instance, the FFR values provided for a coronary artery can be multiplied such that for each coronary artery a combined FFR value is determined, wherein, if several coronary arteries feed the same portion of the myocardium, the FFR values determined for these coronary arteries can be combined, for instance, averaged, in order to determine a single FFR value for the coronary arteries assigned to the same portion of the myocardium. Moreover, a myocardial perfusion value is determined for each portion of the myocardium by combining the myocardial perfusion values of the distribution 25 of myocardial perfusion values. For instance, the myocardial perfusion values provided for a portion of the myocardium can be averaged for determining for each portion of the myocardium a single myocardial perfusion value. Furthermore, in this embodiment the correspondence determining unit 19 is adapted to determine a degree of correspondence between the myocardial perfusion value determined for a portion of the myocardium and the FFR value determined for the one or several coronary arteries assigned to the portion of the myocardium by comparing the FFR value with a first threshold and the myocardial perfusion value with a second threshold. In particular, the correspondence rules can define that a larger degree of correspondence is determined, if a) the FFR value is smaller than a first threshold and the myocardial perfusion value is smaller than a second threshold or b) the FFR value is larger than the first threshold and the myocardial perfusion value is larger than the second threshold, and that a smaller degree of correspondence is determined, if a) the FFR value is larger than the first threshold and the myocardial perfusion value is smaller than the second threshold or b) the FFR value is smaller than the first threshold and the myocardial perfusion value is larger than the second threshold. The first threshold is preferentially the average of the distribution 24 of FFR values and the second threshold is preferentially the average of the distribution 25 of myocardial perfusion values. However, also other first and second thresholds may be used, which may be predetermined, particularly based on calibration procedures. For instance, the first threshold may be 0.6, whereas the second threshold may be defined by the average of the distribution 25 of myocardial perfusion values, in particular, by the average of iodine uptake in the myocardium. In an embodiment the degree of correspondence can be a binary degree of correspondence, wherein it can be determined that the respective FFR value and the respective myocardial perfusion value correspond to each other, if a) the FFR value is smaller than a first threshold and the myocardial perfusion value is smaller than a second threshold or b) the FFR value is larger than the first threshold and the myocardial perfusion value is larger than the second threshold, and that they do not correspond to each other, if a) the FFR value is larger than the first threshold and the myocardial perfusion value is smaller than the second threshold or b) the FFR value is smaller than the first threshold and the myocardial perfusion value is larger than the second threshold. However, the correspondence determining unit 19 may also be adapted to distinguish between more than two different degrees of correspondence.

If the FFR value determined for the one or several coronary arteries assigned to the same portion of the myocardium corresponds to the myocardial perfusion value determined for the portion of the myocardium, the distribution of FFR values along the one or several arteries and the distribution of myocardial perfusion values within the portion of the myocardium can be regarded as corresponding to each other. If for all assignments between portions of the myocardium and the respective one or several coronary arteries it has been determined that the respective values correspond to each other, also the overall distribution of the FFR values and the overall distribution of the myocardial perfusion values can be regarded as corresponding to each other.

Normally, it would be expected that coronary arteries with low FFR values are hemodynamically significant and therefore correlate with low myocardial perfusion values, particularly with low iodine uptake, in the corresponding portions of the myocardium. However, since the determination of the FFR values can be error-prone, clinical decisions can be made with higher confidence, if a low FFR value for a stenosis can be verified by comparing it with the perfusion characteristics of the feeding territory of the artery. The degree of correspondence between the respective FFR value and the respective myocardial perfusion value indicates therefore the reliability of the respective FFR value.

The imaging system 22 further comprises an input unit 20 like a keyboard, a computer mouse, a touch screen, et cetera and a display 21. The input unit 20 and the display 21 could also be regarded as being parts of the processing apparatus. The display 21 displays the coronary arteries and/or the portions of the myocardium and indications being indicative of the determined degrees of correspondence at the respective locations of the coronary arteries and/or of the portions of the myocardium, respectively. In particular, a first kind of indications may be shown on the display 21 at locations of the coronary arteries and/or of the portions of the myocardium, at which the respective determined degree of correspondence is smaller than a correspondence threshold, and/or a second kind of indications may be shown on the display 21 at locations of the coronary arteries and/or of the portions of the myocardium, at which the respective determined degree of correspondence is larger than the correspondence threshold. If the degree of correspondence is a binary degree of correspondence, which may be "1", if the values correspond to each other, and "0", if the values do not correspond to each other, the correspondence threshold may be "0.5". For each stenosis a mark like a colored circle may be displayed indicating if its FFR value is confirmed by the myocardial perfusion information, or if there is conflicting information, i.e., for instance, if the FFR value determined for the coronary artery having the stenosis does not correspond to the myocardial perfusion value determined for the portion of the myocardium being fed by the coronary artery, the stenosis may be marked accordingly.

Figure 5:
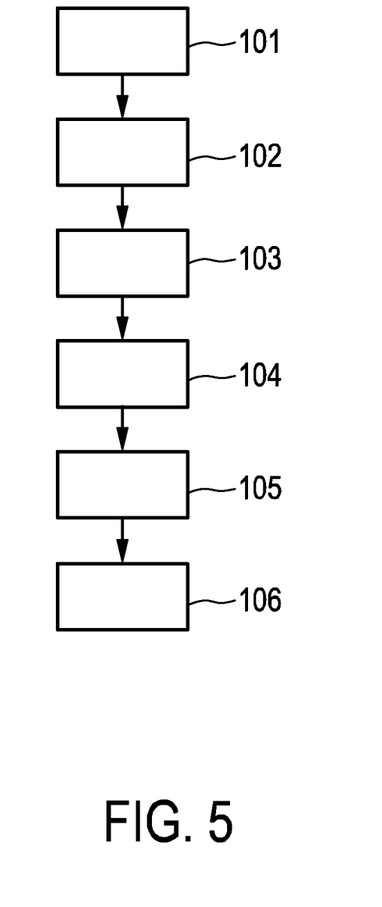
FIG. 5 shows a flowchart exemplarily illustrating an embodiment of an imaging method for imaging the heart of a living being, and FIG. 6 schematically and exemplarily shows an embodiment of a processing apparatus for processing cardiac data.

In the following an embodiment of an imaging method for imaging a heart of a living being will exemplarily be described with reference to a flowchart shown in FIG. 5. In step 101 a first image of the heart being indicative of the FFR of different coronary arteries of the person and a second image of the heart being indicative of the myocardial perfusion of different portions of the myocardium of the person are generated. In particular, the image generation device 23 generates a coronary CTA image as a first image and a spectral CT image as the second image.

In step 102 a distribution 24 of FFR values being indicative of the FFR of different coronary arteries of the person is determined based on the first image. In particular, a three-dimensional geometric model is derived from the CTA image and a simulation of the FFR distribution in the coronary artery tree is performed based on the three-dimensional geometric model of the coronary artery tree, in order to determine the FFR values. In step 103 a distribution 25 of myocardial perfusion values being indicative of the myocardial perfusion of different portions of the myocardium of the person is determined based on the second image. In particular, a three-dimensional iodine map is obtained from the spectral CT image and used as the distribution 25 of myocardial perfusion values.

In step 104 assignments between coronary arteries and portions of the myocardium of the person are determined, wherein the assignments define which portion of the myocardium is fed by which one or several coronary arteries. Preferentially, a model-based heart segmentation and a standardized heart model are used for mapping the individual coronary arteries to their feeding territories in the myocardium. In step 105 degrees of correspondence between the FFR values and the myocardial perfusion values are determined based on the distribution 24 of FFR values, the distribution 25 of myocardial perfusion values and the assignments between the coronary arteries and portions of the myocardium, and in step 106 the coronary arteries and/or the portions of the myocardium are displayed together with indications being indicative of the determined degrees of correspondence at the respective locations of the coronary arteries and/or of the portions of the myocardium, respectively. For instance, for each stenosis a mark like a colored circle can be displayed indicating, if its FFR value is confirmed by the myocardial perfusion information, or if there is conflicting information.

Steps 102 to 105 are steps of processing cardiac data of the person, i.e., for instance, of the distribution of FFR values and the distribution of myocardial perfusion values, and can therefore be regarded as being steps of a processing method for processing cardiac data of a person.

For displaying the coronary arteries the coronary CTA image, the determined three-dimensional geometry of the coronary artery tree or another image of the coronary arteries can be shown on the display 21. For displaying the portions of the myocardium an image of the heart with segmented portions of the myocardium, which are fed by different coronary arteries, can be shown on the display 21.

For the assessment of coronary artery disease it is important to locate stenoses, measure their size, i.e., for instance, the reduction in diameter, and estimate the impact on blood supply in the feeding territories of the heart muscle. The goal is to finally treat only stenoses having a significant impact on hemodynamics. The above described imaging system with the integrated processing apparatus indicates to the physician, for which stenosis reliable FFR values and/or myocardial perfusion values have been determined, in order to allow the physician to use only reliable values for determining whether the respective stenosis has a significant impact on hemodynamics. The myocardial perfusion values are indicative of the perfusion characteristics of the muscle tissue and can, for example, be provided by providing a time-to-peak or area-under-curve map, which can be determined based on dynamic CT myocardial perfusion imaging, or by providing iodine maps, which can be determined by spectral CT imaging. The distributions of myocardial perfusion values preferentially indicate, where blood supply to the muscle is insufficient, but these distributions do not take into account the coronary arteries. The FFR values are indicative of the pressure drop caused by a stenosis and can be determined by simulating the pressure distribution based on a provided three-dimensional geometry of the coronary artery tree of the person.

Displaying combined FFR and perfusion information allows a physician to identify critical stenosis more accurately. The described systems and methods may be applied in CT angiography and myocardial perfusion imaging for the assessment of low and medium risk coronary artery disease patients.

Figure 6:
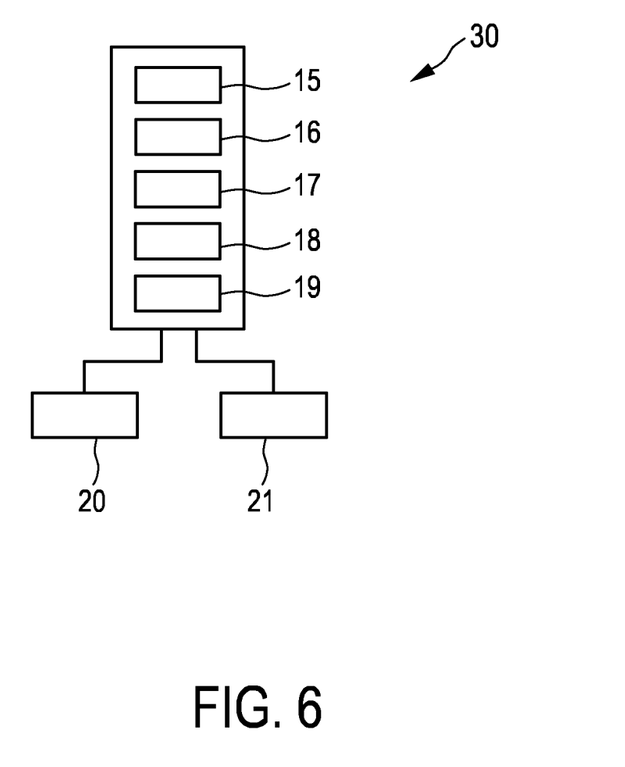

Although in the embodiment described above with reference to FIG. 1 the processing apparatus is integrated in the imaging system, the processing apparatus can also be a standalone apparatus as schematically and exemplarily illustrated in FIG. 6. In this example the processing apparatus 30 for processing cardiac data comprises the FFR providing unit 15, the myocardial perfusion providing unit 16, the heart model providing unit 17, the assignments providing unit 18, the correspondence determining unit 19, the input unit 20 and the display 21. The FFR providing unit 15 can be adapted to determine the distribution of FFR values based on an image of a heart of a person received from an imaging system. However, the FFR providing unit 15 may also just be a storing unit, in which the distribution of FFR values is stored already and from which the stored distribution of FFR values can be retrieved for providing the same. Also the myocardial perfusion providing unit 16 can be adapted to determine the distribution of myocardial perfusion values based on an image received from an imaging system, or the myocardial perfusion providing unit 16 can be a storing unit, in which the distribution of myocardial perfusion values is stored already and from which the distribution of myocardial perfusion values can be retrieved for providing the same. The assignments providing unit 18 can also be adapted to determine the assignments between coronary arteries and portions of the myocardium of the living being based on, for instance, a cardiac model and a provided three-dimensional geometry of the coronary artery tree of the person, or the assignments providing unit 18 may just be a storing unit, in which the assignments are stored already and from which the assignments can be retrieved for providing the same. In the latter case the processing apparatus may not comprise the heart model providing unit 17.

Although in the embodiment described above with reference to FIG. 1 the image generation device 23 is adapted to provide CT images, which are used for determining the distribution of FFR values and the distribution of myocardial perfusion values, i.e. although in the embodiment described above with reference to FIG. 1 images of the same imaging modality are used for determining the distribution of FFR values and the distribution of myocardial perfusion values, in other embodiments also images of different imaging modalities can be used for determining the distribution of FFR values and the distribution of myocardial perfusion values. Thus, the same or different imaging modalities may be used for determining the distribution of FFR values and the distribution of myocardial perfusion values. For instance, the distribution of FFR values may be determined based on a magnetic resonance image, an intravascular ultrasound image, an x-ray CT image et cetera, and the distribution of myocardial perfusion values may be determined based on a positron emission tomography image, a single photon emission CT image, a magnetic resonance image, an x-ray CT image et cetera.

Although in above described embodiments the FFR values are determined based on an image, in another embodiment the FFR values may be determined in another way, for instance, they may directly be measured.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the FFR values, the determination of the myocardial perfusion values, the determination of the assignments between portions of the myocardium and coronary arteries, the determination of the degrees of correspondence between FFR values and myocardial perfusion values, et cetera performed by one or several units or devices can be performed by any other number of units or devices. For example, steps 102 to 105 can be performed by a single unit or by any other number of different units. These procedures and/or the control of the imaging system in accordance with the imaging method and/or the control of the processing apparatus in accordance with the processing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a processing apparatus for processing cardiac data of a living being and to an imaging system comprising the processing apparatus. A distribution of FFR values being indicative of the FFR of different coronary arteries of the living being, a distribution of myocardial perfusion values like values of an iodine map being indicative of the myocardial perfusion of different portions of the myocardium of the living being and assignments between coronary arteries and portions of the myocardium of the living being are used for determining degrees of correspondence between FFR values and myocardial perfusion values. This allows for, for example, a determination of the reliability of the FFR values, if the myocardial perfusion values are known to be reliable, based on the determined degrees of correspondence.

The invention claimed is:

1. A processing apparatus for processing cardiac data of a living being, the processing apparatus comprising:
   a fractional flow reserve providing unit, implemented by a computer, that provides a distribution of fractional flow reserve values being indicative of the fractional flow reserve of different coronary arteries of the living being,
   a myocardial perfusion providing unit, implemented by the computer, that provides a distribution of myocardial perfusion values being indicative of the myocardial perfusion of different portions of the myocardium of the living being,
   an assignments providing unit, implemented by the computer, that provides assignments between coronary arteries and portions of the myocardium of the living being, wherein the assignments define which portion of the myocardium is fed by which coronary artery,
   a correspondence determining unit, implemented by the computer, that determines degrees of correspondence between fractional flow reserve values and myocardial perfusion values based on the distribution of fractional flow reserve values, the distribution of myocardial perfusion values and the assignments between the coronary arteries and portions of the myocardium.

2. The processing apparatus as defined in claim 1, wherein the fractional flow reserve providing unit is adapted to determine the distribution of fractional flow reserve values based on a provided three-dimensional geometry of the coronary artery tree.

3. The processing apparatus as defined in claim 2, wherein the processing apparatus further comprises a heart model providing unit for providing a cardiac model, wherein the cardiac model models at least different portions of the myocardium fed by different coronary arteries, wherein the assignments providing unit is adapted to register the cardiac model to the provided three-dimensional geometry of the coronary artery tree for determining the assignments between coronary arteries and portions of the myocardium.

4. The processing apparatus as defined in claim 1, wherein the myocardial perfusion providing unit is adapted to provide a three-dimensional iodine map obtained from a spectral computed tomography measurement or an area-under-curve map obtained from a dynamic myocardial perfusion computed tomography measurement as the distribution of myocardial perfusion values.

5. The processing apparatus as defined in claim 1, wherein the distribution of fractional flow reserve values defines a fractional flow reserve value for one or several coronary arteries assigned to the same portion of the myocardium and wherein the distribution of myocardial perfusion values defines a myocardial perfusion value for the portion of the myocardium, wherein the correspondence determining unit is adapted to determine a degree of correspondence between the fractional flow reserve value and the myocardial perfusion value by comparing the fractional flow reserve value with a first threshold and the myocardial perfusion value with a second threshold, wherein
   a larger degree of correspondence is determined, if a) the fractional flow reserve value is smaller than the first threshold and the myocardial perfusion value is smaller than the second threshold or b) the fractional flow reserve value is larger than the first threshold and the myocardial perfusion value is larger than the second threshold, and
   a smaller degree of correspondence is determined, if a) the fractional flow reserve value is larger than the first threshold and the myocardial perfusion value is smaller than the second threshold or b) the fractional flow reserve value is smaller than the first threshold and the myocardial perfusion value is larger than the second threshold.

6. The processing apparatus as defined in claim 5, wherein the first threshold depends on the distribution of fractional flow reserve values and/or the second threshold depends on the distribution of myocardial perfusion values.

7. The processing apparatus as defined in claim 6, wherein the first threshold depends on the average of the distribution of fractional flow reserve values and/or the second threshold depends on the average of the distribution of the myocardial perfusion values.

8. The processing apparatus as defined in claim 1, wherein the processing apparatus further comprises a display for displaying the coronary arteries and/or the portions of the myocardium and for displaying indications being indicative of the determined degrees of correspondence at the respective locations of the coronary arteries and/or of the portions of the myocardium, respectively.

9. The processing apparatus as defined in claim 8, wherein the processing apparatus is adapted such that a first kind of indications is shown on the display at locations of the coronary arteries and/or of the portions of the myocardium, at which the respective determined degree of correspondence is smaller than a correspondence threshold, and/or a second kind of indications is shown on the display at locations of the coronary arteries and/or of the portions of the myocardium, at which the respective determined degree of correspondence is larger than the correspondence threshold.

10. The processing apparatus as defined in claim 1, wherein the fractional flow reserve providing unit is adapted to determine the distribution of fractional flow reserve values based on a first image of the heart of the living being generated by a first imaging modality and wherein the myocardial perfusion providing unit is adapted to determine the distribution of myocardial perfusion values based on a second image of the heart of the living being generated by a second imaging modality being different to the first imaging modality.

11. An imaging system for imaging a heart of a living being, the imaging system comprising:

X-ray detector of an image generation device for generating a first image of the heart being indicative of the fractional flow reserve of different coronary arteries of the living being and for generating a second image of the heart being indicative of the myocardial perfusion of different portions of the myocardium of the living being, a processing apparatus as defined in claim 1, wherein the fractional flow reserve providing unit is adapted to determine the distribution of fractional flow reserve values based on the first image and wherein the myocardial perfusion providing unit is adapted to determine the distribution of myocardial perfusion values based on the second image, a display for displaying the coronary arteries and/or the portions of the myocardium and for displaying indications being indicative of the determined degrees of correspondence at the respective locations of the coronary arteries and/or of the portions of the myocardium, respectively.

12. A processing method for processing cardiac data of a living being, the processing method comprising:

providing a distribution of fractional flow reserve values being indicative of the fractional flow reserve of different coronary arteries of the living being, providing a distribution of myocardial perfusion values being indicative of the myocardial perfusion of different portions of the myocardium of the living being, providing assignments between coronary arteries and portions of the myocardium of the living being, wherein the assignments define which portion of the myocardium is fed by which coronary artery, determining degrees of correspondence between fractional flow reserve values and myocardial perfusion values based on the distribution of fractional flow reserve values, the distribution of myocardial perfusion values and the assignments between the coronary arteries and portions of the myocardium.

13. An imaging method for imaging a heart of a living being, the imaging method comprising:

generating a first image of the heart being indicative of the fractional flow reserve of different coronary arteries of the living being and generating a second image of the heart being indicative of the myocardial perfusion of different portions of the myocardium of the living being, determining degrees of correspondence between fractional flow reserve values and myocardial perfusion values as defined in claim 12, wherein the distribution of fractional flow reserve values is provided by determining fractional flow reserve values based on the first image and the distribution of myocardial perfusion values is provided by determining myocardial perfusion values based on the second image, displaying the coronary arteries and/or the portions of the myocardium and displaying indications being indicative of the determined degrees of correspondence at the respective locations of the coronary arteries and/or of the portions of the myocardium, respectively.

14. A non-transitory computer readable medium encoded with a computer program for processing cardiac data of a living being, the computer program comprising program code means for causing a processing apparatus, to carry out the steps of the processing method as defined in claim 12, when the computer program is run on a computer controlling the processing apparatus.

15. A non-transitory computer readable medium encoded with a computer program for imaging a heart of a living being, the computer program comprising program code means for causing an imaging system, to carry out the steps of the imaging method as defined in claim 13, when the computer program is run on a computer controlling the processing apparatus.

* * * * *